US005954750A

United States Patent [19]

Steffensmeier

[11] Patent Number: 5,954,750

[45] Date of Patent: Sep. 21, 1999

[54] DROP MECHANISM FOR CHIROPRACTIC TABLE

[76] Inventor: Lloyd A. Steffensmeier, 102-122 W. Main St., Lisbon, Iowa 52253

[21] Appl. No.: 08/907,127

[22] Filed: Aug. 6, 1997

[51] Int. Cl.[6] .................... A61F 5/00

[52] U.S. Cl. .................... 606/237; 606/242; 606/245

[58] Field of Search .................... 606/237, 238, 606/241, 242, 245

[56] References Cited

U.S. PATENT DOCUMENTS 4,856,497 8/1989 Westphal .................... 606/242

5,259,396 11/1993 Lipari .................... 606/242

*Primary Examiner*—Michael Buiz

*Assistant Examiner*—Vy Q. Bui

*Attorney, Agent, or Firm*—James C. Nemmers

[57] ABSTRACT

A chiropractic table having an improved drop mechanism using two pair of roller bearings or other devices and a T-shaped or other bracket with the upright stem of the bracket being combined with detents including an adjustable spring loaded ball. The chiropractic table further provides a unique arrangement in which the chest and lumbar sections are combined into a single support section which is in turn hinged to the pelvic section with a separate drop mechanism provided for the combination chest lumbar section and the pelvic section.

4 Claims, 2 Drawing Sheets

FIG. 3
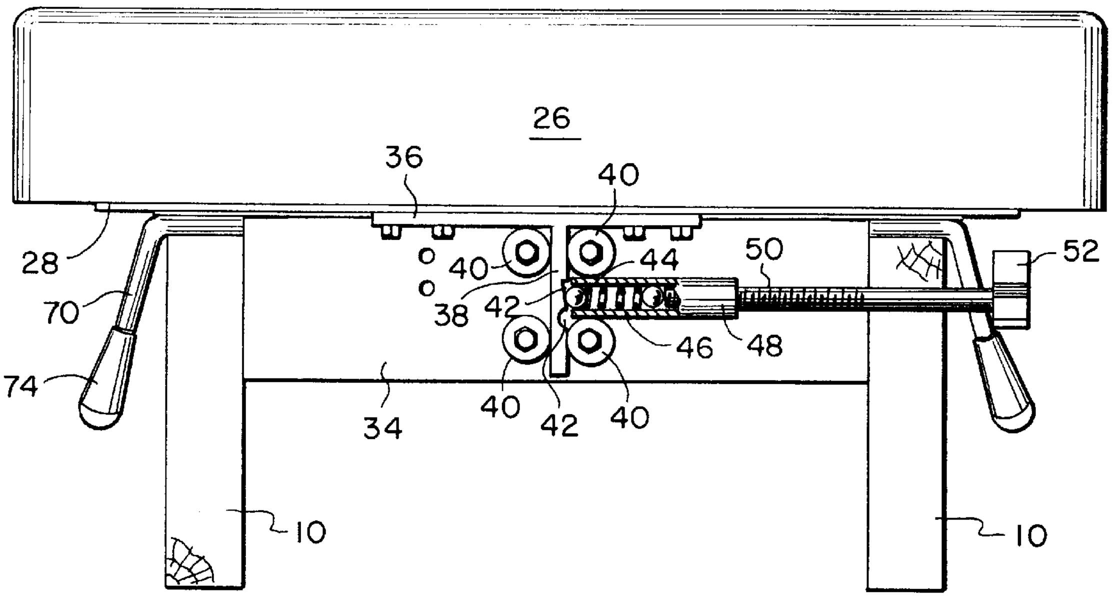
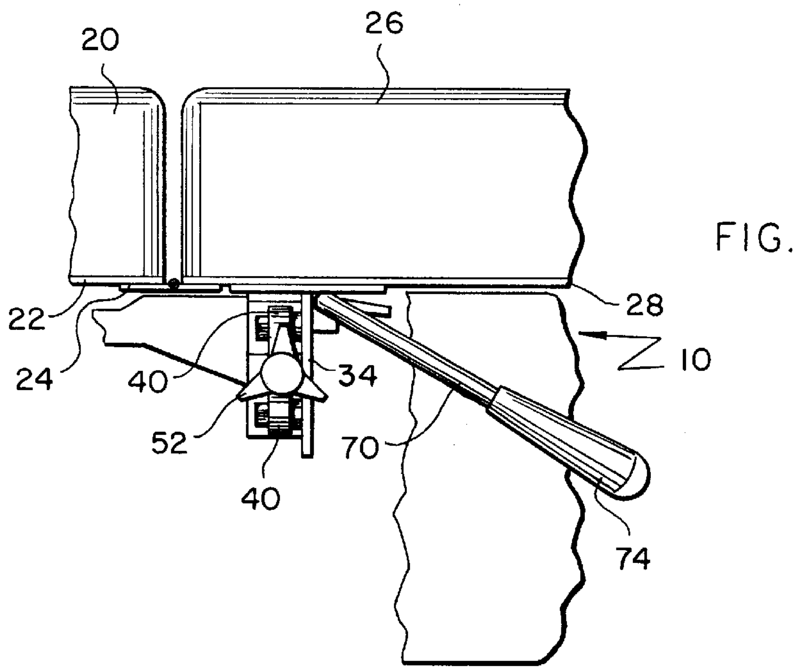
FIG. 4

DROP MECHANISM FOR CHIROPRACTIC TABLE

BACKGROUND OF THE INVENTION

There are known and commercially available to the practicing chiropractor and other health professionals numerous types of tables to assist the health professional in conducting examinations, adjustments and treatments beneficial to the patient. When used for chiropractic adjustments, these tables commonly are designed so that the patient support is separated into separate sections for the head, chest, lumbar, pelvic and foot sections. Commonly, each of these sections is independently supported and some are moveable so that the health professional can conduct the desired adjustment or treatment. Some of the sections have a moveable mechanism that allows that section to be displaced a predetermined distance to facilitate the adjustment. In other tables of this type, the movement of the sections is controlled manually, pneumatically or hydraulically, and various systems have been devised to assist the health care professional in applying the correct amount of force so as to provide the desired therapeutic benefit for the patient. One example of such a table is disclosed in my prior U.S. Pat. No. 4,960,111.

In tables that do not employ hydraulics or pneumatics to control movement of the individual sections, the sections typically are supported on a vertical bar or tube mounted in guides with a spring loaded ball and detent arrangement. With the prior art drop mechanisms, the amount of force necessary to cause the drop depends upon where the health professional pushes on the section. With the prior art arrangement, it is difficult for the health professional to determine, except by experience and feel, the correct amount of force that should be applied to the patient since it will depend upon where on the patient support section the force is applied.

Moreover, in all of the known prior art tables of this type, each of the support sections, the chest, lumbar, and pelvic, are totally independent of each other and require three separate drop mechanisms. This not only adds to the overall cost of the table, but since each drop mechanism can be adjusted as to the amount of force required to create the drop, the health professional must adjust each independently. There is therefore room for improvement in the drop mechanism itself as well as the way in which the various sections are mounted on the table. It is therefore an object of the invention to provide an improved drop mechanism for tables of this type and to provide a unique and improved arrangement whereby the number of drop mechanisms can be reduced while still providing the capability of allowing the health professional to conduct the necessary adjustments more easily and consistently.

SUMMARY OF THE INVENTION

The chiropractic table of the invention provides an improved drop mechanism using two pair of roller bearings and a T-shaped bracket with the upright stem of the T-shaped bracket being combined with detents including an adjustable spring loaded ball. The chiropractic table of the invention further provides a unique arrangement in which the chest and lumbar sections are combined into a single support section which is in turn hinged to the pelvic section with a separate drop mechanism provided for the combination chest lumbar section and the pelvic section.

BRIEF DESCRIPTION OF THE DRAWING

FIG. 3 is an end elevational view of the pelvic section; and

FIG. 4 is a side elevational view of a portion of the pelvic and chest sections.

DESCRIPTION OF THE PREFERRED EMBODIMENT OF THE INVENTION

Figure 1:
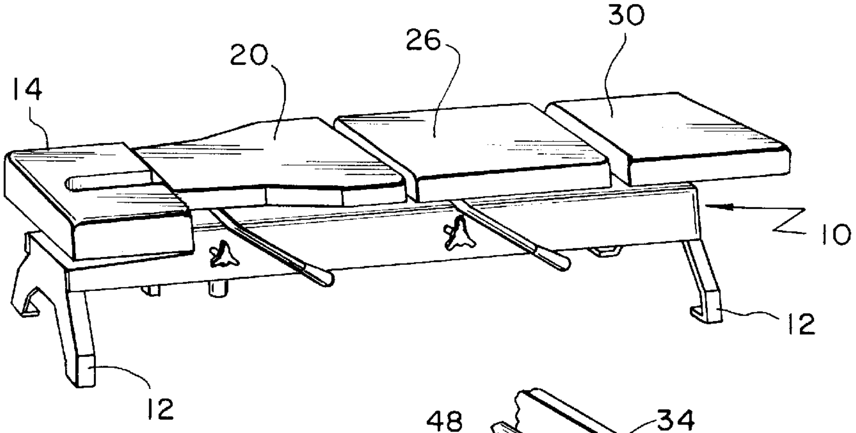
FIG. 1 is a perspective view of a chiropractic table constructed according to the principles of the invention.

The invention relates to and is employed in connection with a patient support such as a table which is used for the examination or treatment of the patient. The preferred embodiment is described in connection with a chiropractic table that has separate patient support sections. Referring to the drawings, and especially FIGS. 1 and 2, there is illustrated a chiropractic table of the side-posture type which has a table frame 10 supported by legs 12. At the head end of the table is a head section 14 secured by hinges 16 to a transverse member 18 that forms a part of the frame 10. The head section 14 and all the other patient support sections described hereinafter are preferably cushioned for the comfort of the patient. A chest-lumbar section 20 includes a mounting board 22 (see FIG. 4) to which one side of a hinge 24 is affixed. A pelvic section 26 is similarly mounted on a mounting board 28, and the other side of hinge 24 is affixed to the mounting board 28 at the front end of pelvic section 26, and the other end of the pelvic section 26 is secured to hinge 32 which is in turn attached to the cross member 33 of frame 10. The foot section 30 is fixed directly to the frame 10 in any suitable manner.

Figure 2A:
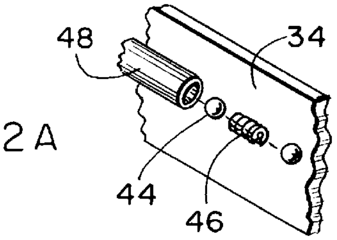
FIG. 2 is an exploded view showing the support and mounting components for the various sections of the chiropractic table of the invention.
Figure 2:
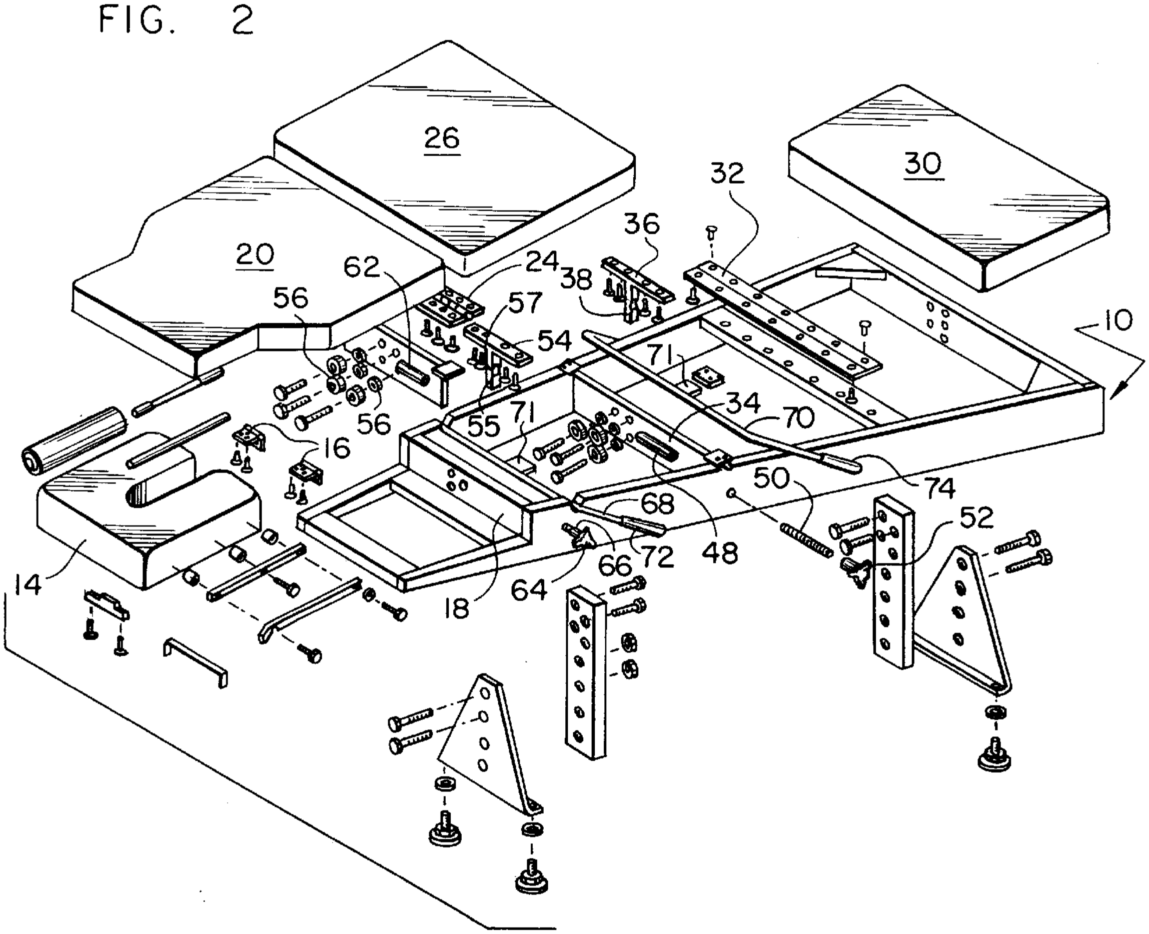

Referring now to FIGS. 2, 3 and 4, the pelvic section 26 has secured to its mounting board 28 and extending down from it a mounting plate 34. Affixed in any suitable manner on the forward side of the mounting plate 34 is a T-bracket 36 or other suitable bracket the depending leg 38 of which is engaged between two pair of roller bearings 40 or other suitable anti-friction guides that are also affixed to the mounting plate 34. The depending leg 38 of T-bracket 36 is provided with two indentations 42 which are engageable with a ball 44 biased by spring 46 to form a detent arrangement. The ball 44 and spring 46 are contained in a hollow tube 48 secured to the side of mounting plate 34. The outer end of tube 48 is threaded to receive a threaded member 50 having a handle 52. This allows the tension of the detent arrangement to be adjusted.

A similar support arrangement is provided for the chest-lumbar section 20 which includes a T-bracket 54 having a depending leg 55 that extends between roller bearings 56. The indentations 57 are combined with a ball and spring (not shown) contained in tube 62 to provide an adjustable detent arrangement the tension of which can be varied by turning the handle 64 at the outer end of the threaded member 66.

In order to move each section upwardly and thus cock it in preparation for a drop, a cocking bar 68 extends beneath the chest-lumbar section 20 and a similar cocking bar 70 extends beneath the pelvic section 26. Each of the cocking bars 68 and 70 has a tab 71 near the center, which tab 71 engages the mounting board 22 or 28 of the chest section 20 or pelvic section 26, respectively. Handles 72 and 74 are provided at the outer ends of the cocking bars 68 and 70 so that the health professional can lift the handle to raise the tab 71 on the cocking bar and thus raise the section in preparation for a drop. When the pelvic section 26, for example, is raised by lifting on cocking handle 74, the T-bracket 36 will move upwardly until the ball 44 is positioned in the lower one of the indentations 42. Then, when the health professional is ready to conduct the procedure utilizing the drop, the health presses downwardly on that part of the patient's body being supported on the section that is to be dropped. When sufficient force is applied by the health professional, the pelvic section, for example, will drop thus releasing the ball 44 from the lower one of the indentations 42 and placing it into the upper one of the indentations 42. With the drop mechanism of the invention, a more consistent force can be applied to any portion of a section to produce the required drop in the section. Moreover, by making the chest-lumbar section a single section and hinging it to the pelvic section, only two drop mechanisms are necessary rather than three as in prior art structures. This unique arrangement simplifies and thus lowers the overall cost of the table, and with the unique drop mechanism of the invention, the health professional can apply a more consistent force to any part of a section where the drop is to be produced. With prior art arrangements, the force would vary depending upon where the health professional applied the force to the section or the patient lying on the section. The invention thus provides for consistency in practicing various procedures.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

What is claimed is as follows:

1. A chiropractic table having an improved drop mechanism for treating patients lying on the table, said table comprising: a supporting frame having a head end and a foot end; patient supporting sections mounted on the frame between the head end and the foot end, said patient supporting sections including a head section, a pelvic section, a combination chest-lumbar section in which the chest-lumbar section is hinged to the pelvic section, and a foot section; a hinge connecting the chest-lumbar section to the pelvic section; a first drop mechanism operatively combined with the combined chest-lumbar-pelvic section; a second drop mechanism operatively combined with the pelvic section, the drop mechanisms providing for controlled movement of each section from an upper position to a lower position; means to manually raise the sections to the upper position in preparation for a drop to the lower position; each drop mechanism including a support bracket affixed to a section; a vertical member affixed to and extending downwardly from the support bracket and having vertically extending spaced-apart sides; an upper pair of roller bearings engageable with the vertical member, one bearing on each of the sides of the vertical member; and a lower pair of roller bearings engageable with the vertical member, one bearing on each of the sides of the vertical member, one of the sides of the vertical member having an upper indentation and a lower indentation therein; a ball adapted to be engaged with the indentations to lock the vertical member and thus the section to which it is attached in either the upper or the lower position; and a spring biasing the ball into one of the indentations.

2. The chiropractic table of claim 1 in which there is adjustment means combined with the spring and ball for varying the spring force on the ball.

3. A drop mechanism for a chiropractic table for treating patients lying on the table, said table including a supporting frame and patient supporting sections mounted on the frame with each section moveable from an upper position to a lower position, said drop mechanism comprising: means to raise a selected section to an upper position, a support bracket affixed to the selected section, a vertical member affixed to and extending downwardly from the support bracket and having vertically extending spaced-apart sides, an upper pair of roller bearings engageable with the vertical member, one bearing on each of the sides of the vertical member, a lower pair of roller bearings engageable with the vertical member, one bearing on each of the sides of the vertical member, one of the sides of the vertical member having an upper indentation and a lower indentation therein, a ball adapted to be engaged with the indentations to lock the vertical member and thus the section to which it is attached in either the upper or the lower position, and a spring biasing the ball into one of the indentations.

4. The drop mechanism of claim 3 in which there is adjustment means combined with the spring and ball for varying the spring force on the ball.

* * * * *